(12) United States Patent
Vanderby et al.

(10) Patent No.: US 7,744,535 B2
(45) Date of Patent: Jun. 29, 2010

(54) METHOD AND APPARATUS FOR ACOUSTOELASTIC EXTRACTION OF STRAIN AND MATERIAL PROPERTIES

(75) Inventors: Ray Vanderby, Madison, WI (US); Hirohito Kobayashi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 349 days.

(21) Appl. No.: 11/549,865

(22) Filed: Oct. 16, 2006

(65) Prior Publication Data

US 2007/0089530 A1  Apr. 26, 2007

Related U.S. Application Data

(63) Continuation-in-part of application No. 11/192,930, filed on Jul. 29, 2005.

(60) Provisional application No. 60/592,746, filed on Jul. 30, 2004.

(51) Int. Cl.
*A61B 8/00* (2006.01)

(52) U.S. Cl. .................. 600/438; 600/437; 600/442; 600/443; 600/448; 310/311

(58) Field of Classification Search .......... 600/437, 600/438, 442, 443, 448; 310/311
See application file for complete search history.

(56) References Cited

U.S. PATENT DOCUMENTS 5,107,837 A    4/1992  Ophir
5,293,870 A  *  3/1994  Ophir et al. .................. 600/437
7,022,077 B2 *  4/2006  Mourad et al. ............... 600/449
2005/0043623 A1  2/2005  Jurvelin et al.
2006/0025682 A1  2/2006  Vanderby et al.

OTHER PUBLICATIONS

PCT International Search Report, PCT/US07/81515, Mailed May 8, 2008, ISA/US, Alexandria, Virginia, USA.

Hakulinen, M. A. et al., Ability of Ultrasound Backscattering to Predict Mechanical Properties of Bovine Trabecular Bone, Ultrasound in Medicine and Biology, pp. 919-927, Jul. 1, 2004, vol. 30, No. 7, Elsevier, New York, NY, USA.

Bengtsson, Johan, Supplementary European Search Report, Sep. 17, 2009, European Patent Office, The Hague, The Netherlands.

Kish, James M., "Final Office Action" for U.S. Appl. No. 11/192,930, dated Aug. 4, 2009, Notice of References Cited, United States Patent and Trademark Office, Alexandria, VA, USA.

(Continued)

*Primary Examiner*—Brian Casler
*Assistant Examiner*—James Kish
(74) *Attorney, Agent, or Firm*—Boyle Fredrickson, S.C.

(57) ABSTRACT

An ultrasound machine processes ultrasonic data according to acoustoelastic properties of the materials to obtain strain information without specific assumptions with respect to the material properties of the measured material or a variety of different material properties normally not obtained by ultrasound machines.

18 Claims, 5 Drawing Sheets

OTHER PUBLICATIONS

Takahashi et al., "Stress Dependency on the Ultrasonic Wave Velocity and Attenuation of Fe-C System," 1996, Journal De Physique IV, vol. 6, pp. C8845-C8848, EDP Sciences, Les Ulis Cedex, France.

MacDonald, Douglas, "On Determining Stress and Strain and Texture using Ultrasonic Velocity Measurements," 1981, IEEE Transaction on Sonics and Ultrasonics, vol. SU-28, No. 2, pp. 75-79, New York, New York, USA.

Prosser, William, "Stress Dependence of Ultrasonic Velocity in Unidrectional Graphite/Epoxy Composites for Longitudinal Waves Propagating Along the Direction of Stress," Review of Progress in Quantitative Nondestructive Evaluation, 1990, vol. 9, pp. 17101-17107, Springer, New York, New York.

* cited by examiner

METHOD AND APPARATUS FOR ACOUSTOELASTIC EXTRACTION OF STRAIN AND MATERIAL PROPERTIES

CROSS-REFERENCE TO RELATED APPLICATIONS

The present application is a continuation-in-part of U.S. application Ser. No. 11/192,930, filed Jul. 29, 2005, which claims the benefit of U.S. Provisional Application 60/592,746 filed Jul., 30, 2004 hereby incorporated by reference.

STATEMENT REGARDING FEDERALLY-SPONSORED RESEARCH OR DEVELOPMENT

This invention was made with United States government support awarded by the following agency: NIH AR049266. The United States government has certain rights in this invention.

BACKGROUND OF THE INVENTION

The present invention relates to ultrasonic imaging and quantitative measurements and, in particular, to an improved apparatus and method for making ultrasonic measurements of material strain and stiffness.

Conventional ultrasonic imaging provides a mapping of ultrasonic echo signals onto an image plane where the intensity of the echo, caused principally by relatively small differences in material properties between adjacent material types, is mapped to brightness of pixels on the image plane. While such images serve to distinguish rough structure within the body, they provide limited insight into the physical properties of the imaged materials.

Ultrasonic elastography is a new ultrasonic modality that may produce data and images revealing stiffness properties of the material, for example, strain under an externally applied stress, Poisson's ratio, Young's modulus, and other common strain and strain-related measurements.

In one type of elastography, termed "quasi-static" elastography, two images of a material in two different states of compression, for example, no compression and a given positive compression, may be obtained by the ultrasound device. The material may be compressed by a probe (including the transducer itself) or, for biological materials, by muscular action or movement of adjacent organs. Strain may be deduced from these two images by computing gradients of the relative shift of the material in the two images along the compression axis. Quasi-static elastography is analogous to a physician's palpation of tissue in which the physician determines stiffness by pressing the material and detecting the amount of material yield (strain) under this pressure.

The process of deducing the shift in material under compression may start by computing local correlations between the images, and then evaluating differences in echo arrival time for correlated structures before and after compression. Differences in echo arrival time are converted to material displacement (or strain, which is displacement normalized by length) at different points within the material by multiplying the difference in arrival times by the speed of sound through the material.

The amount of material strain indirectly provides an approximate measure of stiffness. Material that exhibits less strain under compression may be assumed to be stiffer, while material that exhibits more strain under compression is assumed to be less stiff.

The parent application to the present application provided a new paradigm of strain measurement which, rather than deducing strain by measuring the motion of the material, deduced strain directly from the modification of the ultrasonic signal caused by changes in the acoustic properties of the material under deformation (acoustoelasticity). A similar technique could be used, if the strain is known, to derive the material properties.

BRIEF SUMMARY OF THE INVENTION

The present inventors have now realized that acoustoelastic analysis can provide both strain and material properties from a set of ultrasonic signals without the need to know one to derive the other. A similar technique can be used to provide a variety of new material property measurements including stiffness gradient (the change in stiffness with strain), tangential modulus, Poisson's ratio, and wave signal attenuation (all as a function of strain) as well as tissue density that in turn can be used to provide images and novel data describing materials. These measurements, in the medical field, may help differentiate tissue types that otherwise would appear similar in standard or elastographic ultrasound images.

Specifically then, one embodiment of the present invention provides an ultrasound system having an ultrasound transducer assembly for transmitting an ultrasound signal to collect a first and second echo signals when the material is at a first and second tension applied across the axis of the ultrasound. A processor receives the first and second echo signals from the ultrasound transducer and processes the signals according to a stored program to deduce both strain of the material and its stiffness.

Thus, it is one feature of at least one embodiment of the invention to provide for measurements of strain in materials in situations where the functional loading cannot be easily characterized. It is another feature of at least one embodiment of the invention to allow simultaneous measurement of strain and material properties (stiffness, density, Poisson's ratio, tangential modulus and wave attenuation) without error-prone precharacterization of the material.

The processor may determine strain and material properties (stiffness, Poisson's ratio, tangential modulus and wave attenuation) from a time of flight of ultrasound between the first and second interfaces in the target material and the reflection coefficients indicating reflected ultrasonic energy at the first and second interfaces.

Thus, it is another feature of at least one embodiment of the invention to extract quantitative information from the strength of reflections that allows improved analysis of ultrasonic signals.

In another embodiment, the present invention provides an ultrasonic acoustoelastography system that evaluates the first and second echo signals at multiple states of deformation to provide a measure of change in stiffness as a function of deformation and uses this change in material properties (stiffness, density, Poisson's ratio, tangential modulus and wave attenuation) as a function of deformation to characterize the material.

Thus, it is one feature of at least one embodiment of the invention to use a measure of the deviation of stiffness from constant, assumed in other elastographic techniques, in fact, to characterize tissue.

The echo signals may be from boundaries of the material in another material, or the reverse, or of the material in a uniform transmission material such as water.

Thus, it is one feature of at least one embodiment of the invention to provide a method of obtaining the necessary signals in a variety of situations.

The change of stiffness or other material properties (density, Poisson's ratio, tangential modulus and wave attenuation) may be output as an image.

Thus, it is one feature of at least one embodiment of the invention to provide a new imaging mode.

In a preferred embodiment, the invention provides a system for measuring material properties with ultrasound, which measures the strength of reflected waves from multiple levels of deformation of the material at a first and second boundary of the material and measures the time of travel of the waves between the first and second boundary. These two measurements are combined to deduce material strain, and then other material properties (stiffness, tangential modulus, Poisson's ratio, wave attenuation, and density) can be calculated using the deduced strain and measured wave signal sets from multiple states of material deformation.

Thus, it is one feature of at least one embodiment of the invention to provide a wealth of new measurable qualities of materials using ultrasound.

These particular objects and advantages may apply to only some embodiments falling within the claims, and thus do not define the scope of the invention.

DETAILED DESCRIPTION OF THE PREFERRED EMBODIMENT

Figure 1:
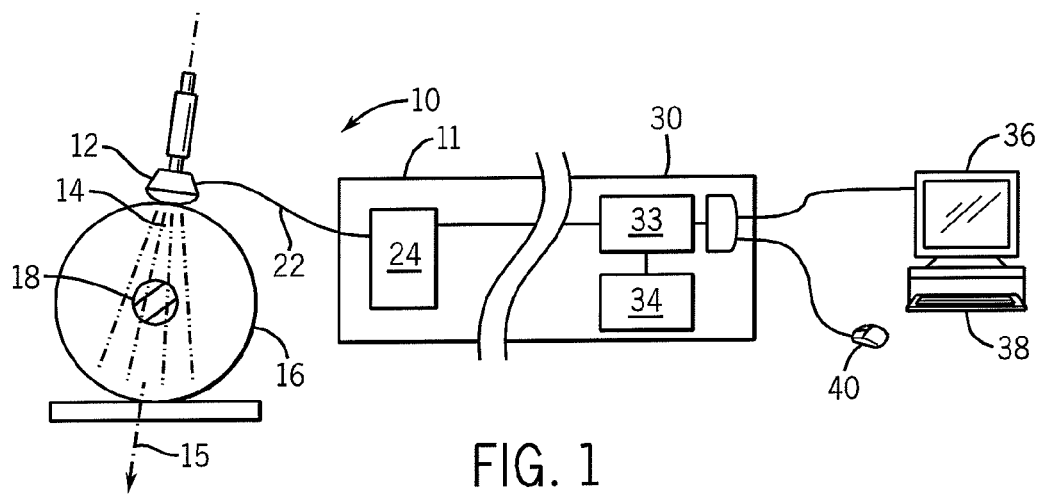
FIG. 1 is a simplified block diagram of an ultrasound scanner suitable for use with the present invention having a transducer system providing compression of a measured material along the beam of ultrasound.

Referring now to FIG. 1, an acoustoelastographic ultrasound system 10 suitable for use with the present invention may employ an ultrasonic imaging machine 11 alone or in combination with an external computer 30. Generally, the ultrasonic imaging machine 11 provides the necessary hardware and/or software to collect and process ultrasonic echo signals by processor 33 held within the ultrasonic imaging machine 11 or in the external computer 30.

An ultrasonic transducer 12 associated with the ultrasonic imaging machine 11 may transmit an ultrasound beam 14 along an axis 15 toward a region of interest 18 within a patient 16 to produce echo signals returning generally along axis 15. The echo signals may be received by the ultrasonic transducer 12 and converted to an electrical echo signal. For the construction of an image, multiple rays within ultrasound beam 14 and corresponding echo signals will be acquired within a region of interest surrounding for example a tumor 18. In one embodiment, the transducer 12 may include a force measuring transducer to quantify force applied to the patient from the transducer 12 when the transducer 12 is being used to apply compression to the patient 16.

Multiple acquisitions of echo signals may be obtained with the tissue of the patient 16 in different states of compression, the compression being performed most easily by pressing the ultrasonic transducer 12 into the tissue of the patient 16 along axis 15. Other compression techniques, including those using independent compressor paddles or muscular action of tissue, may also be used.

The electrical echo signals communicated along lead 22 may be received by interface circuitry 24 of the ultrasonic imaging machine 11. The interface circuitry 24 provides amplification, digitization, and other signal processing of the electrical signal as is understood in the art of ultrasonic imaging. The digitized echo signals are then transmitted to a memory 34 for storage and subsequent processing by a processor 33, as will be described below.

After processing, the echo signals may be used to construct an image displayed on graphical display 36 or may be displayed quantitatively on the graphical display 36. Input commands affecting the display of the echo signals and their processing may be received via a keyboard 38 or cursor control device 40, such as a mouse, attached to the processor 33 via interface 24, as is well understood in the art.

Figure 2:
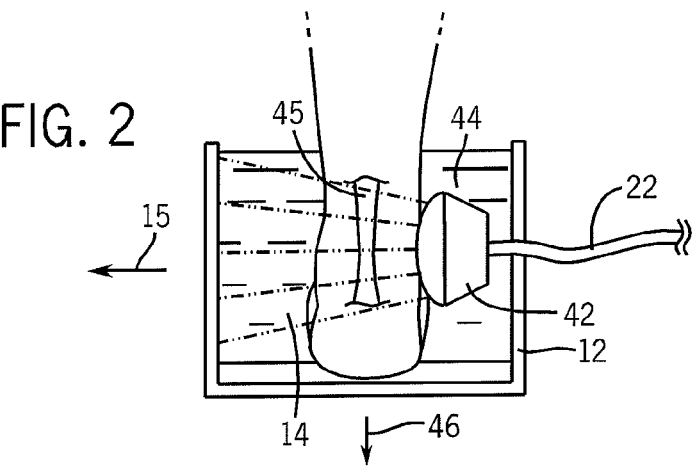
FIG. 2 is a fragmentary view of an alternative transducer system used with tension on the material applied across the beam of ultrasound.

Referring now to FIG. 2, in an alternative embodiment, the ultrasonic transducer 12 may be placed, for example in a container 42 holding a coupling medium 44 with known material properties, such as water. A portion of the patient's body, in this case the patient's heel including a tendon 45, may be immersed in the coupling medium 44 so that the ultrasonic transducer 12 directs an ultrasound beam 14 generally along a horizontal axis 15 through the tendon 45 which extends vertically across the axis 15. In this case, the tendon 45 is essentially adjacent to the ultrasonic transducer 12 separated only by a small amount of skin and tissue and a thin layer of the coupling medium 44.

Echo signal, as described above, may be obtained with the tendon in different states of tension, for example by instructing the patient to press down on the ball of the foot down to lift against the patient's weight during one acquisition set. The tension is applied vertically along axis 46 generally perpendicular and crossing axis 15. As before the echo signals are provided over lead 22 to the interface circuitry 24.

Figure 3:
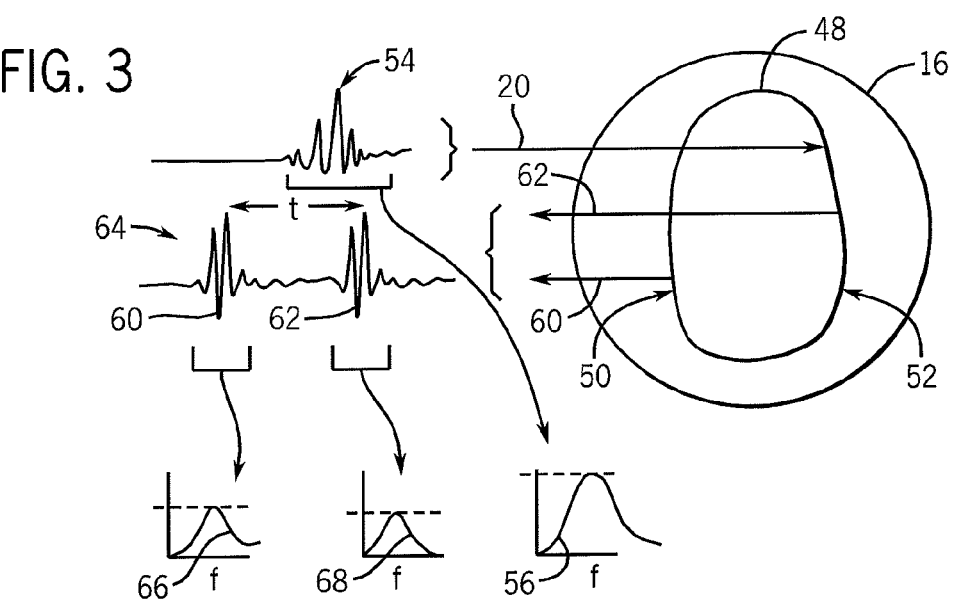
FIG. 3 is an elevational cross-section of material being measured using the devices of FIG. 1 or 2, showing the incident and reflected signal and the analysis of the reflected signal to deduce time of flight and reflection coefficients.

Referring now to FIG. 3, in both the applications of FIGS. 1 and 2, incident ultrasound rays 20 of the ultrasound beam 14 are directed toward an internal body structure 48 to cross a front interface 50 and rear interface 52 of the body structure. The front interface 50 and rear interface 52 may, for example, be interfaces between different tissues or materials within a patient 16 or interfaces between a coupling material and the body structure 48.

The incident ultrasound ray 20 will typically be a pulse signal 54 having a first frequency spectrum 56. The passage of the incident ultrasound ray 20 through the front interface 50 will cause a first reflected ultrasound ray 60 to be returned to the transducer 12 from the front interface 50. Similarly, the passage of the ray 20 through the rear interface 52 will cause a second reflected ultrasound ray 62 to the transducer 12 from the rear interface 52. These two reflected ultrasound rays combine with other rays to produce a return signal 64 having two dominant pulses associated with the reflected ultrasound rays 60 and 62, each having a corresponding frequency spectrum: spectrum 66 for the ray 60, and spectrum 68 for the ray 62.

These pulses may be readily identified by amplitude peak detection techniques or adaptive filtering, implemented by the processor 33 executing a stored program, so that a travel time t may be determined by measuring the time between these pulses 60 and 62, such as indicates the travel time of the incident ultrasound ray 20 between the front interface 50 and the rear interface 52.

The processor 33 may further analyze the frequency spectra 56, 66, and 68 to determine reflection coefficients at each of the interfaces 50 and 52 indicating generally how much of the incident ultrasound ray 20 was reflected at each interface 50 and 52. The reflection coefficients, may, for example, be determined by comparing the peak amplitude of spectra 56 against the peak amplitudes of spectra 66 and 68, respectively, as will described further below.

Acoustoelastic Strain Gauge (ASG)

Figure 4:
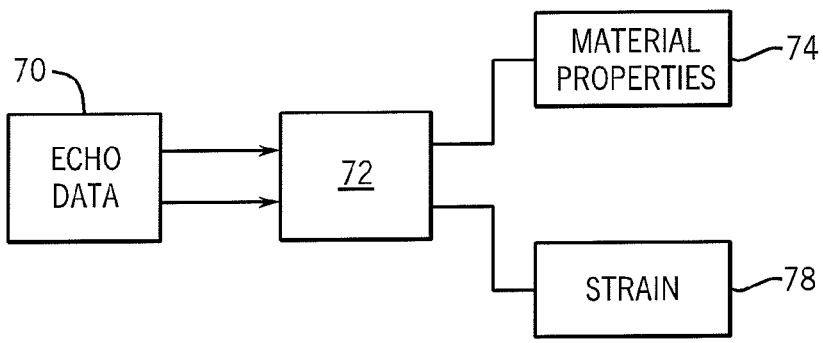
FIG. 4 is a block diagram of the calculations of the present invention using the system of FIG. 2 to simultaneously obtain stiffness and strain.

Referring now to FIG. 4, the echo data 70 comprising signals 54 and 64 for two states of tension, per FIG. 1, may be collected and provided to a processing program 72 contained in the memory 34 and executed by processor 33. From these data, acceptably without additional measurement or input with respect to the material being measured, a stiffness value or material property 74 and a strain measurement 78 may both be determined, for example, for the tendon 45 of FIG. 2. This contrasts to the method of the parent of the present application in which one of the material properties 74 or strain 78 is needed to be known to produce the other.

Figure 5:
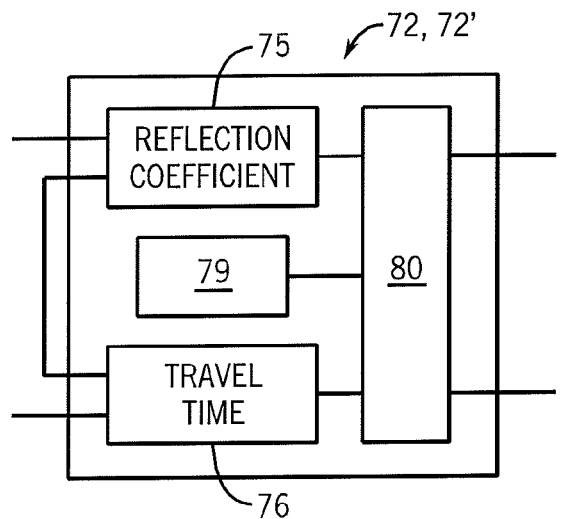
FIG. 5 is a detailed view of the calculation block of FIG. 4 showing the extraction of reflection coefficients and time of flight, per FIG. 3, in this process.

Referring to FIG. 5, the program 72, as described above, generally provides for a determination of the reflection coefficient 75 and the travel time 76, as described below, for these two states of tension of the tissue, and makes certain general assumptions 79 about the measured materials which are processed as follows.

Frequency Domain Analysis

First, the transverse stiffness (e.g., along the ultrasound axis 15) is assumed to be some function of the applied strain e, for example, a general second order function such as:

$$\tilde{C}_{33}(e) \approx C_2 \cdot e^2 + C_1 \cdot e + C_{33} \tag{1}$$

As will be discussed later, the order or the form of this function is not critical and is chosen so that it can be fit to the data.

By introducing the assumption of near incompressibility (i.e. the material density does not depend on the amount of strain or deformation) it follows that:

$$\rho^S(e) \approx \rho^S(e=0) = \rho_0^S, \tag{2}$$

Under these assumptions, the wave velocity through thickness (in transverse direction) is given by:

$$V(e_i) = \sqrt{\frac{\tilde{C}_{33}(e)}{\rho^S(e)}} \approx \sqrt{\frac{\tilde{C}_{33}(e)}{\rho_0^S}}. \tag{3}$$

The reflection coefficient at the interface of surrounding medium (e.g., water) and target medium is defined by:

$$R(e) = \frac{\rho^S V(e) - \rho^W V^W}{\rho^S V(e) + \rho^W V^W}$$

or re-organized form $$\rho^S \cdot V(e_i) = \frac{1 + R(e_i)}{1 - R(e_i)} \rho^W \cdot V^W. \tag{4}$$

In these relations, superscripts S and W respectively represent the target tissue (solid) and the surrounding medium (e.g., water).

Combining eq. (1)–(4), a relation between material properties ($C_1, C_2, C_{33}, \rho_0$) and impedance square (right hand side of equation) for each stretched state is derived as:

$$\rho_0^S(C_2 \cdot e^2 + C_1 \cdot e + C_{33}) = \left[\frac{(1+R(e))}{(1-R(e))}\rho^W V^W\right]^2 = IPS(e) \tag{5}$$

When the material properties of the surrounding medium (e.g., water) are known, the reflection coefficient can be retrieved from measured echo signals, and the impedance square parameter on the right hand side is known. As will be noted below, however, knowledge of the material properties of the surrounding material is not required.

Similarly, the relation between the material property and impedance square at non-stretched state can be derived as:

$$\rho_0^S C_{33} = \left[\frac{(1+R_0)}{(1-R_0)}\rho^W V^W\right]^2 = IPS_0. \tag{6}$$

By the taking the ratio of reflection information eqs. (5) and (6), the unknown target tissue density cancels and is eliminated as a parameter required to determine the other material properties. This is important because in-vivo tissue density is very difficult to measure.

$$\frac{\rho_0^S(e)\tilde{C}_{33}(e)}{\rho_0^S C_{33}} \approx \frac{C_2 \cdot e^2 + C_1 \cdot e}{C_{33}} + 1 = \frac{\left[\frac{(1+R(e))}{(1-R(e))}\rho^W V^W\right]^2}{\left[\frac{(1+R_0)}{(1-R_0)}\rho^W V^W\right]^2} \tag{7}$$

$$= \frac{\left[\frac{(1+R(e))}{(1-R(e))}\right]^2}{\left[\frac{(1+R_0)}{(1-R_0)}\right]^2} = \frac{IPS(e)}{IPS_0}$$

Here, the left hand side term represents the unknown normalized material property. Again, the right hand side is measured or known information. Since the material properties of the surrounding medium ($\rho^W V^W$) are cancelled out in the same process, the material properties of the surrounding medium that were originally assumed to be known are also not essential to the analysis.

Time Domain Analysis:

The travel time at e=0 (non-stretched state) can be related to tissue thickness D and wave velocity $V_0$ by:

$$T_0 = \frac{2D}{V_0} 2D\sqrt{\frac{\rho_0^s}{C_{33}}}. \tag{8}$$

Similarly, the travel time at e≠0 (stretched state) is given by:

$$T(e_i) = \frac{2d(e_i)}{V(e_i)}. \tag{9}$$

Here, the wave velocity V and tissue thickness d at a stretched state are given by:

$$V \approx \sqrt{\frac{\tilde{C}_{33}(e)}{\rho_0^s}} = \sqrt{\frac{C_2 e^2 + C_1 e + C_{33}}{\rho_0^s}} \tag{10}$$

and $$d(e_i) = \frac{D}{\sqrt{1+e_i}}. \tag{11}$$

By taking the ratio of the wave travel time eq.(10) and (11):

$$\left(\frac{T_0}{T(e)}\right)^2 = \left(\frac{2D/V_0}{2d/V}\right)^2 = \left(\sqrt{\frac{\tilde{C}_{33}(e)}{C_{33}}}\sqrt{1+e}\right)^2 = \frac{IPS(e)}{IPS_0}(1+e) \tag{12}$$

the strain e applied to the tissue can be evaluated as:

$$e = \frac{IPS_0}{IPS(e)}\left(\frac{T_0}{T(e)}\right)^2 - 1 \tag{13}$$

Since the right hand side of this relation contains parameters that are measured directly from wave signals, the applied strain can be evaluated directly without any supplemental information. Once the applied strains are evaluated, they are used in equation (7) to compute the normalized stiffness.

$$\frac{C_2 \cdot e^2 + C_1 \cdot e}{C_{33}} + 1 = \frac{\left[\frac{(1+R(e))}{(1-R(e))}\right]^2}{\left[\frac{(1+R_0)}{(1-R_0)}\right]^2} = \frac{IPS(e)}{IPS_0} \tag{7}$$

If the density of the target tissue $\rho_0^S$ is known prior to the testing, the coefficients in the transverse stiffness function can be directly evaluated by substituting the evaluated strain into relation (5)

$$C_2 \cdot e^2 + C_1 \cdot e + C_{33} = \frac{1}{\rho_0^s}\left[\frac{(1+R(e))}{(1-R(e))}\rho^W V^W\right]^2 = \frac{1}{\rho_0^s} IPS(e) \tag{5'}$$

Once the transverse stiffness is given as a function of applied strain e, the tissue thickness at any strain level can be calculated from relation (9)

$$d(e) = \frac{T(e)}{2}V(e) = \frac{T(e)}{2}\sqrt{\frac{C_2 \cdot e^2 + C_1 \cdot e + C_{33}}{\rho_0^s}} \tag{14}$$

Implementation

Step 1. Measure the reflected echo signal and compute impedance square $IPS_0$ and wave travel time $T_0$ through thickness in the non-stretched (unloaded) state (e=0).

If the density of target tissue is known or can be assumed with reasonable accuracy, the stiffness at the non-deformed state can be given by (4).

$$C_{33} = \frac{1}{\rho_0^s}\left[\frac{(1+R(e))}{(1-R(e))}\rho^W V^W\right]^2 = \frac{1}{\rho_0^s} IPS_0$$

Step 2a. Stretch the tissue and measure the reflected echo signal and compute $IPS(e_1)$ and wave travel time $T(e_1)$. From relation (13), evaluate the applied strain $e_1$.

Step 2b. Repeat step 2a for the second stretched state to evaluate $IPS(e_2)$ and wave travel time $T(e_2)$ through thickness. From relation (13), evaluates the applied strain $e_2$.

Step 3. Set up the following two independent equations, by substituting evaluated strains $e_1$ and $e_2$ into relation (7).

If density is not known:

For strain $e_1$:

$$\frac{C_2 \cdot e_1^2 + C_1 \cdot e_1}{C_{33}} + 1 = \frac{IPS(e_1)}{IPS_0}$$

For strain $e_2$:

$$\frac{C_2 \cdot e_2^2 + C_1 \cdot e_2}{C_{33}} + 1 = \frac{IPS(e_2)}{IPS_0}$$

If the density is known, substitute strains $e_1$, $e_2$ and stiffness $C_{33}$ evaluated from previous relation (5)

For strain $e_1$:

$$C_2 \cdot e_1^2 + C_1 \cdot e_1 + C_{33} = \frac{1}{\rho_0^s} IPS(e_1)$$

For strain $e_2$:

$$C_2 \cdot e_2^2 + C_1 \cdot e_2 + C_{33} = \frac{1}{\rho_0^s} IPS(e_2)$$

Step 4. Evaluate two normalized unknown parameters $C_1/C_{33}$ and $C_2/C_{33}$ for the case of unknown tissue density or stiffness parameters $C_1$ and $C_2$ for the case of known tissue density by solving above system of equations simultaneously.

With wave signals acquired at two different unknown stretched states ($e_1$ and $e_2$) and with wave signals from the non-stretched state (e=0), we can evaluate applied strain and two normalized stiffness coefficients ($C_1/C_{33}$ and $C_2/C_{33}$) without any prior information or we can evaluate $C_1$ and $C_2$ when tissue density is known.

In the above example, stiffness was assumed to be a second order function of applied strain. It is possible, however, to use the same technique to evaluate strain and stiffness coefficients even if stiffness is a higher order (or a different type) of function of strain. Unless, it is not possible to acquire wave signals at multiple strain states, a higher order assumption of stiffness does not cause any difficulty for this technique.

For example, if stiffness turns out to be a third order function of strain ($\tilde{C}_{33}(e) \approx C_3 \cdot e^3 + C_2 \cdot e^2 + C_1 \cdot e + C_{33}$), it requires only one extra wave signal measurement to set up the required extra equations. If N+1 sets of signals (N wave signals measured at different stretch levels and one wave signal from non-stretched state) can be acquired, N unknown normalized material coefficients can be evaluated. Therefore, the Nth order normalized transverse stiffness $\tilde{C}_{33}(e)/C_{33} \approx (C_N/C_{33} \cdot e^N + \ldots C_1/C_{33} \cdot e + 1)$ can be found.

It is worth noting the differences between the method of "elastography" and the ASG technique presented herein. Since "elastography" uses only the wave equation (and does not use the acoustoelastic equation done in this analysis), changes in tissue acoustic characteristics as a function of strain do not show up in elastographic analysis. Hence the stiffness is always treated as fixed number i.e. $\tilde{C}_{33}(e) = C_{33}$. As a result, the frequency domain relation (7) becomes, $$\frac{\rho_0^S(e)\tilde{C}_{33}(e)}{\rho_0^S C_{33}} \approx \frac{\rho_0^S C_{33}}{\rho_0^S C_{33}} = 1 \neq \frac{\left[\frac{(1+R(e))}{(1-R(e))}\right]^2}{\left[\frac{(1+R_0)}{(1-R_0)}\right]^2} = \frac{IPS(e)}{IPS_0}.$$

Therefore the relationship between reflection coefficients cannot be utilized in "elastography". In addition, the time domain relation (13) suffers from the same fixed stiffness $\tilde{C}_3(e) = C_{33}$ as:

$$\hat{e} = \left(\frac{T_0}{T(e)}\right)^2 - 1.$$

This oversimplified relation in time domain indicates that the applied strain can never correctly account for strain dependent signals within the framework of "elastography". The differences between the two methods are tabulated in Table 1.

TABLE 1

|  | Frequency domain Relation (7) | Time domain relation (13) | Variables that can be evaluated |
|---|---|---|---|
| ASG | $\frac{C_2 \Box e^2 + C_1 \Box e}{C_{33}} + 1 = \frac{IPS(e)}{IPS_0}$ | $e = \frac{IPS_0}{IPS(e)}\left(\frac{T_0}{T(e)}\right)^2 - 1$ | Normalized coefficients $C_1/C_{33}, \ldots, C_N/C_{33}$ for unknown density or coefficients $C_1, \ldots, C_N$ for known tissue density. & applied strain e |
| Elastography |  | $\hat{e} = \left(\frac{T_0}{T(e)}\right)^2 - 1$ | Approximate strain $\hat{e}$ |

Stiffness Gradient Identification (SGI)

Figure 6:
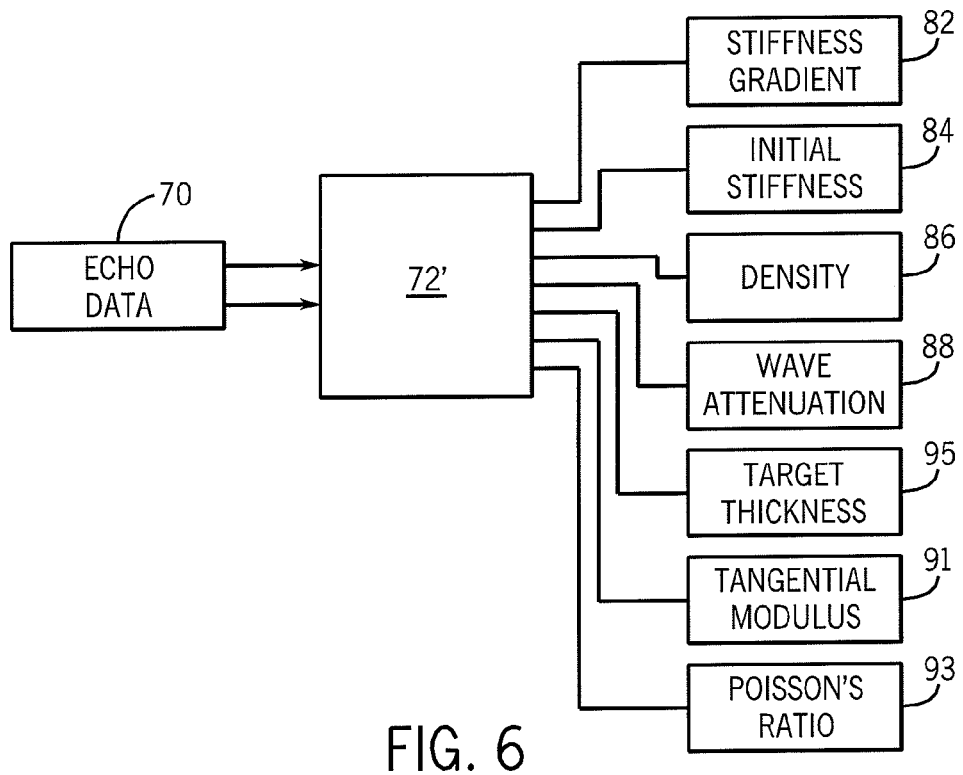
FIG. 6 is a block diagram of the calculations of the present invention using the system of FIG. 1 to simultaneously obtain different material properties and tissue strain.

Referring now to FIG. 6, the echo data 70 comprising signals 54 and 64 from multiple states of compression per, FIG. 1, may be collected and provided to a processing program 72' contained in the memory 34 and executed by processor 33. The echo data 70 may be processed by a program 72', similar to program 72 described with respect to FIG. 4, to produce a variety of different measurements, including stiffness gradient 82, tangential modulus 91, initial stiffness 84, density 86, Poisson's ratio 93, target thickness 95, and wave attenuation 88.

Referring to FIG. 5, the program 72', as described above, generally provides for a determination of the reflection coefficient 75 and the travel time 76, as described below, for these two states of compression of the tissue, and makes certain general assumptions 79 about the measured materials which are processed as follows.

The following analysis will consider a one-dimensional three-layered model (surrounding medium 1/target medium 2/surrounding medium 1). The material properties in the surrounding medium are assumed to be known. If not, an additional medium (coupling material) with known properties can be added artificially. The method can then analyze the surrounding medium properties first and then use those properties for analysis of the target tissue. Hence this technique can be applied to a multi-layered medium. If the size of the ultrasound wave width is relatively small compared to the size of the target tissue, this assumption can be applied to two dimensions as well.

If only the normalized tissue stiffness is required, following relations and steps may be followed.

Frequency Domain Analysis:

First, based on the theory of acoustoelasticity, the wave velocities in the compressed medium 1 (surrounding tissue) and medium 2 (target tissue) are given by:

$$V_1(e_i) \approx \sqrt{\frac{C_1(e_i) + t_1(e_i)}{\rho_1}} \text{ and } V_2(e_i) \approx \sqrt{\frac{C_2(e_i) + t_2(e_i)}{\rho_2}}. \quad (101)$$

Here, C(e) and t(e) represent strain (e) dependent stiffness and stress. Subscripts represent the medium numbers.

By substituting above relations into the well known definition of a reflection coefficient:

$$R(e_i) = \frac{\rho_2 \cdot V_2(e_i) - \rho_1 \cdot V_1(e_i)}{\rho_2 \cdot V_2(e_i) + \rho_1 \cdot V_1(e_i)} \text{ or} \quad (102)$$

$$\rho_2 \cdot V_2(e_i) = \frac{1 + R(e_i)}{1 - R(e_i)} \rho_1 \cdot V_1(e_i),$$

The unknown parameters in target tissues in the $i^{th}$ compressed state will be given by:

$$\rho_2[C_2(e_i) + t_2(e_i)] = \left[\frac{1 + R(e_i)}{1 - R(e_i)}\right]^2 \rho_1[C_1(e_i) + t_1(e_i)]. \quad (103)$$

With consideration of stress continuity ($t_1(e_i) = t_2(e_i)$) that is guaranteed in a one-dimensional model, relation (103) can be further simplified to:

$$\rho_2 C_2(e_i) \approx \left[\frac{1 + R(e_i)}{1 - R(e_i)}\right]^2 \rho_1 C_1(e_i). \quad (104)$$

Here, the material density of mediums 1 and 2 are assumed to be very close $\rho_1 \approx \rho_2$.

The unknown parameters in target tissues in a non-compressed state are derived to be:

$$\rho_2 C_2(e_i = 0) = \left[\frac{1 + R(e_i = 0)}{1 - R(e_i = 0)}\right]^2 \rho_1 C_1(e_i = 0). \quad (105)$$

Now assume stiffness in target tissue (medium 2) is a second order function of the applied strain e as:

$$C_2(e) \approx a_2 \cdot e^2 + b_2 \cdot e + c_2. \quad (106)$$

By taking the ratio of eq.(104) and (105) and with substitution of relation (106), relation between material property in medium 2 and measured reflection coefficient are given by:

$$\frac{a_2 e_i^2 + b_2 e_i + c_2}{c_2} \approx \frac{\left[\frac{1 + R(e_i)}{1 - R(e_i)}\right]^2 C_1(e_i)}{\left[\frac{1 + R(e_i = 0)}{1 - R(e_i = 0)}\right]^2 C_1(e_i = 0)}. \quad (107)$$

Time Domain Analysis

The travel time at e=0 (non-stretched state) is related to tissue thickness D and wave velocity $V_0$ by:

$$T_0 = \frac{2D}{V_0} = 2D\sqrt{\frac{\rho_2}{C_2}}. \quad (108)$$

Similarly, the travel time at e≠0 (stretched state) is given by:

$$T(e_i) = \frac{2d(e_i)}{V(e_i)}. \quad (109)$$

Here, the wave velocity V and tissue thickness d at stretched state is given by:

$$V \approx \sqrt{\frac{C_2(e)}{\rho_2}} = \sqrt{\frac{a_2 e^2 + b_2 e + c_2}{\rho_2}} \quad (110)$$

and $$d(e_i) = D \cdot (1 - e_i). \quad (111)$$

The ratio of the wave travel time eq.(108) and (109) is given by:

$$\frac{T_0}{T} = \frac{\frac{D}{V_0}}{\frac{d}{V}} \approx \frac{\sqrt{\frac{c_2}{\rho_2}}}{\frac{D(1 - e_i)}{\sqrt{\frac{C_2(e_i) + t_2(e_i)}{\rho_2}}}} \quad (112)$$

$$= \left(\sqrt{\frac{C_2(e_i) + t_2(e_i)}{c_2}}\right) \frac{1}{1 - e}.$$

Since $$\frac{C_2(e_i) + t_2(e_i)}{c_2}$$

is related to reflection coefficients and parameters in medium 1 by:

$$\frac{C_2(e_i) + t_2(e_i)}{c_2} = \frac{\rho_2[C_2(e_i) + t_2(e_i)]}{\rho_2 C_2(e_i = 0)}$$

$$= \frac{\left[\frac{1 + R(e_i)}{1 - R(e_i)}\right]^2 \rho_1[C_1(e_i) + t_1(e_i)]}{\left[\frac{1 + R(e_i = 0)}{1 - R(e_i = 0)}\right]^2 \rho_1 C_1(e_i = 0)}$$

$$= \frac{\left[\frac{1 + R(e_i)}{1 - R(e_i)}\right]^2 [C_1(e_i) + t_1(e_i)]}{\left[\frac{1 + R(e_i = 0)}{1 - R(e_i = 0)}\right]^2 C_1(e_i = 0)}$$

the strain e applied to the tissue will evaluated as:

$$e_i = 1 - \sqrt{\frac{\left[\frac{1 + R(e_i)}{1 - R(e_i)}\right]^2 [C_i(e_i) + t_1(e_i)]}{\left[\frac{1 + R(e_i = 0)}{1 - R(e_i = 0)}\right]^2 C_1(e_i = 0)}} \frac{T}{T_0}. \quad (113)$$

Since the right hand side of this relation contains parameters that are either known or measured directly from wave signals, the applied strain can be evaluated directly without any supplemental information. Once the applied strains are evaluated, they are used in equation (107) to obtain normalized stiffness properties.

$$\frac{a_2 e_i^2 + b_2 e_i + c_2}{c_2} \approx \frac{\left[\frac{1+R(e_i)}{1-R(e_i)}\right]^2 C_1(e_i)}{\left[\frac{1+R(e_i=0)}{1-R(e_i=0)}\right]^2 C_1(e_i=0)} \tag{107}$$

Implementation

Step 1. Compress media with a higher level of known stress for example using a force transducer in the ultrasonic probe.

$$t_2(e_A) = t_1(e_A)$$

This higher stress enhances the contrast between the target medium and the surrounding medium. Since the acoustic contrast is now enhanced, the location and shape of the target tissue can be identified with greater precision. Now, the reflection coefficient for this compressed tissue can be used in the following relation:

$$\rho_2[C_2(e_A) + t_2(e_A)] = \left[\frac{1+R(e_A)}{1-R(e_A)}\right]^2 \rho_1[C_1(e_A) + t_1(e_A)] \text{ or}$$

$$\rho_2 C_2(e_A) \approx \left[\frac{1+R(e_A)}{1-R(e_A)}\right]^2 \rho_1 C_1(e_A)$$

Step 2. Repeat the same measurements for different, but compressive stresses that are smaller than the stress used in the previous step.

$$t_2(e_B) < t_2(e_A)$$

$$\rho_2[C_2(e_B) + t_2(e_B)] = \left[\frac{1+R(e_B)}{1-R(e_B)}\right]^2 \rho_1[C_1(e_B) + t_1(e_B)] \text{ or}$$

$$\rho_2 C_2(e_B) \approx \left[\frac{1+R(e_B)}{1-R(e_B)}\right]^2 \rho_1 C_1(e_B)$$

Step 3. Measure the reflection information for the non-compressed state. In this state, the acoustic contrast between target medium and surrounding medium is typically lowest. Hence the boundary between the two media is less clear. However, by following the compression-enhanced boundary in the previous two steps, the boundary between the two media can be estimated and the reflection coefficient can be computed.

$$\rho_2 C_2(e_i = 0) = \left[\frac{1+R(e_i=0)}{1-R(e_i=0)}\right]^2 \rho_1 C_1(e_i = 0)$$

Step 4. Evaluate applied strain $e_A$ and $e_B$ using the relation (113).

Step 5. With evaluated strain $e_A$ and $e_B$, unknown normalized material properties ($\alpha = a_2/c_2$ and $\beta = b_2/c_2$) can evaluated by solving the following two relations simultaneously. Again, the parameters on the right hand side of the relation are known or measured.

$$\frac{a_2 e_A^2 + b_2 e_A + c_2}{c_2} \approx \frac{\left[\frac{1+R(e_A)}{1-R(e_A)}\right]^2 C_1(e_A)}{\left[\frac{1+R(e_i=0)}{1-R(e_i=0)}\right]^2 C_1(e_i=0)}$$

-continued $$\frac{a_2 e_B^2 + b_2 e_B + c_2}{c_2} \approx \frac{\left[\frac{1+R(e_B)}{1-R(e_B)}\right]^2 C_1(e_B)}{\left[\frac{1+R(e_i=0)}{1-R(e_i=0)}\right]^2 C_1(e_i=0)}$$

Tissue stiffness often is reasonably linear over a functional range of strain and the slope of the stiffness function depends on the tissue type. For such tissues, parameter $\beta$ will be more dominant and important than $\alpha$. Once the slope $\beta$ is evaluated, tissue identification can be performed by checking a table of stiffness slopes for various tissues.

If a full set of material properties (stiffness, stiffness gradient, Poisson's ratio tangential modulus, and density) are to be evaluated, the following additional relations are further required.

In a non-deformed isotropic homogenous material, the Young's modulus E is known to related the stiffness C via material constants termed Poisson's ratio (v) and is given by $$E = \frac{(1+v)(1-2v)}{(1-v)} C \tag{201}$$

Now assume this relation also holds in a deformed state if the deformation is one dimensional and relation between tangential modulus and stiffness can be given by:

$$E(e) = \frac{(1+v(e))(1-2v(e))}{(1-v(e))} C(e) \tag{202}$$

E(e) is termed as tangential modulus instead of Young's modulus for general finite deformation. Since nearly incompressible materials like biological tissues are considered, the Poisson's ratio at deformed state can be assumed to be:

$$v(e) = \frac{1}{2} - \varphi(e) \tag{203}$$

$\phi(e)$ is a small variable that governs small volume changes caused by the compression strain e. After substituting relation (203) into (202), expand (202) as function of $\phi(e)$ and ignoring the higher order term, then relation (202) simplifies to:

$$E(e) \approx 6\phi(e) \cdot C(e) \tag{204}$$

If the stiffness in the target tissue (e.g. tendon 45 in FIG. 2 or tumor 18 in FIG. 1) $C_2(e)$ and $\phi(e)$ can be assumed to be $$C_2(e) = a_2 \cdot e^2 + b_2 \cdot e + c_2 \tag{106}$$

and $$\phi(e) = s_1 + s_2 \cdot e, \tag{205}$$

the tangential modulus in target tissue (e.g. tendon 45 in FIG. 1 or tumor 18 in FIG. 1) can be given as the function of strain as $$E_2(e) \approx 6\phi(e) \cdot C_2(e) = 6s_1 c_2 + (6s_2 c_2 + 6s_1 b_2)e + (6s_2 b_2 + 6s_1 a_2)e^2 + 6s_2 a_2 e^3. \tag{206}$$

Stress under these assumptions (one dimensional deformation) is given by integrating the tangential modulus, $$t_2(e) = \int E(e)de \qquad (207)$$

$$= 6\left[s_1c_2e + \frac{1}{2}(s_2c_2 + s_1b_2)e^2 + \frac{1}{3}(s_2b_2 + s_1a_2)e^3 + \frac{1}{4}s_2a_2e^4\right].$$

With these relations, the key SGI mathematical relations for evaluating full sets of material properties can be derived in following manner.

First, take the ratio of eq.(103) and eq.(105) from previous section as $$\frac{[C_2(e_i) + t_2(e_i)]}{C_2(e_i = 0)} = \frac{\left[\frac{1+R(e_i)}{1-R(e_i)}\right]^2 [C_1(e_i) + t_1(e_i)]}{\left[\frac{1+R(e_i=0)}{1-R(e_i=0)}\right]^2 C_1(e_i=0)} \qquad (208)$$

By substituting (106) and (207) into this relation, (208) is now changed into $$1 + \left(6s_1 + \frac{b_2}{c_2}\right)e + \left(3s_2 + 3s_1\frac{b_2}{c_2} + \frac{a_2}{c_2}\right)e^2 + \qquad (209)$$

$$\left(2s_2\frac{b_2}{c_2} + 2s_1\frac{a_2}{c_2}\right)e^3 + \frac{3}{2}s_2\frac{a_2}{c_2}e^4 = \frac{\left[\frac{1+R(e_i)}{1-R(e_i)}\right]^2 [C_1(e_i) + t_1(e_i)]}{\left[\frac{1+R(e_i=0)}{1-R(e_i=0)}\right]^2 C_1(e_i=0)}$$

Now, this relation (209) can be utilized as frequency domain relation to take the place of relation (107) in previous section.

The implementation of this relation is exactly same as the implementation steps of (107). First, evaluate applied strains $e_1$ from relation (113) at multiple deformed configurations (more than 4 sets of data, each at a different strain). Second, feed back the evaluated strain into relation (209) to evaluate four unknown material constants $$s_1, s_2\frac{b_2}{c_2} \text{ and } \frac{a_2}{c_2}.$$

With these evaluated constants, both deformation dependent Poisson's ratio v(e) and normalized stiffness $NC_2(e)$ are given by $$v(e) = \frac{1}{2} - (s_1 + s_2 \cdot e)$$

and $$NC_2(e) = \frac{a_2}{c_2} \cdot e^2 + \frac{b_2}{c_2} \cdot e + 1.$$

For simplicity, only a one dimensional layered model (surrounding medium-target medium-surrounding medium) is considered in the current description. Here, the condition of stress continuity $t_2(e) = t_1(e)$ is guaranteed at the interface of two different media and $t_1(e)$ is known from measuring the pressure of the ultrasound transducer associated with each deformation. Using this assumption with equation 207 and the strain evaluated for each loading, a set of equations are generated from the relationship below. From these, the two coefficients describing Poisson's ratio, and all three material constants ($a_2$, $b_2$ and $c_2$) required to define target medium stiffness $C_2(e)$ can be determined.

$$t_2(e) = t_1(e)$$

$$= 6\left[s_1c_2e + \frac{1}{2}(s_2c_2 + s_1b_2)e^2 + \frac{1}{3}(s_2b_2 + s_1a_2)e^3 + \frac{1}{4}s_2a_2e^4\right]$$

$$= 6s_1c_2e + 3(s_2c_2 + s_1b_2)e^2 + 2(s_2b_2 + s_1a_2)e^3 + \frac{3}{2}s_2a_2e^4$$

The unknown target tissue density can be also evaluated by utilizing same relation.

First re-organize relation (103) as $$\rho_2 C_2(e_i) = \left[\frac{1+R(e_i)}{1-R(e_i)}\right]^2 \rho_1[C_1(e_i) + t_1(e_i)] - \rho_2 t_2(e_i) \qquad (210)$$

By taking the ratio of (210) and (105), the normalized stiffness of target tissue will be given as $$NC_2(e) = \frac{\rho_2 C_2(e_i)}{\rho_2 C_2(e_i = 0)} = 1 + \frac{b_2}{c_2}e + \frac{a_2}{c_2}e^2 \qquad (211)$$

$$\approx \frac{\left[\frac{1+R(e_i)}{1-R(e_i)}\right]^2 \rho_1[C_1(e_i) + t_1(e_i)] - \rho_2 t_2(e_i)}{\left[\frac{1+R(e_i=0)}{1-R(e_i=0)}\right]^2 \rho_1 C_1(e_i=0)}$$

$$= \frac{\left[\frac{1+R(e_i)}{1-R(e_i)}\right]^2}{\left[\frac{1+R(e_i=0)}{1-R(e_i=0)}\right]^2} \frac{C_1(e_i) + t_1(e_i)}{C_1(e_i=0)} -$$

$$\frac{\rho_2 t_1(e_i)}{\left[\frac{1+R(e_i=0)}{1-R(e_i=0)}\right]^2 \rho_1 C_1(e_i=0)}$$

By substituting (209) into (211), the density ratio between unknown target tissue (medium 2) and unknown surrounding tissue (medium 1) is given as:

$$\rho_{RATIO} = \frac{\rho_2}{\rho_1} \qquad (212)$$

$$= \frac{\left[\frac{1+R_0}{1-R_0}\right]^2 C_1(e_i = 0)}{t_1(e)}$$

$$\left[6s_1e + \left(3s_2 + 3s_1\frac{b_2}{c_2}\right)e^2 + e^3\left(2s_2\frac{b_2}{c_2} + 2s_1\frac{a_2}{c_2}\right)e^4 + \frac{3}{2}s_2\frac{a_2}{c_2}e^4\right]$$

Note four constants $$\left(s_1, s_2 \frac{b_2}{c_2} \text{ and } \frac{a_2}{c_2}\right)$$

on the right hand side have been evaluated in the previous step, hence they are known properties at this stage.

At first glance, in the relation (212), the density ratio may appear to be a function of applied strain e. However, by observing both relation (207) and (212), the density ratio can be shown to a constant as follows.

$$\rho_{RATIO} = \frac{\rho_2}{\rho_1} = \frac{\left[\frac{1+R_0}{1-R_0}\right]^2 C_1(e=0)}{t_1(e)} \frac{t_2(e)}{c_1} \quad (213)$$

$$= \frac{\left[\frac{1+R_0}{1-R_0}\right]^2 C_1(e=0)}{C_2(e=0)}$$

In the process, stress continuity $t_2(e)=t_1(e)$ was introduced.

This relation can be also derived by re-organizing (105). Hence this indicates that the density ratio given by (213) should result in a constant value regardless of the state of deformation. Once the density ratio is evaluated, the density of target tissue can be simply given by $$\rho_2 \rho_{RATIO} = \rho_1 \quad (214)$$

Once the density of target tissue are given, this can be brought back to equation (102) in SGI to evaluate the wave velocity in target tissue at any deformed state $$V_2(e_i) = \frac{1+R(e_i)}{1-R(e_i)} \cdot \frac{\rho_1}{\rho_2} \cdot V_1(e_i) \quad (215)$$

From the evaluated wave velocity, the size (thickness) of target tissue at any deformed state can be also calculated by following relations.

$$d(e_i) = T(e_i) \cdot V_2(e_i)/2 \quad (216)$$

In this relation, $T(e_i)$ represents the round trip wave travel time through target medium.

This thickness can be used in the evaluation of wave attenuation coefficient.

Implementation

Step 1. Compress media with a higher level of known stress $t_1(e_A)$ for example using a force transducer in the ultrasonic probe.

$$t_2(e_A) = t_1(e_A)$$

This higher stress enhances the contrast between the target medium and the surrounding medium. Since the acoustic contrast is now enhanced, the location and shape of the target tissue can be identified with greater precision. Now, the reflection coefficient for this compressed tissue can be used in the following relation:

$$c_2 + (6s_1 + b_2)e_A + (3s_2c_2 + 3s_1b_2 + a_2)e_A^2 +$$
$$(2s_2b_2 + 2s_1a_2)e_A^3 + \frac{3}{2}s_2a_2e_A^4 = \left[\frac{1+R(e)}{1-R(e)}\right]^2 [C_1(e_A) + t_1(e_A)]$$

Step 2. Repeat the same measurements for different, but compressive stresses ($t_1(e_B)$, $t_1(e_C)$ and $t_1(e_D)$) that are smaller than the stress used in the previous step.

$$t_1(e_B) = t_2(e_B) < t_2(e_A)$$
$$c_2 + (6s_1 + b_2)e_B + (3s_2c_2 + 3s_1b_2 + a_2)e_B^2 +$$
$$(2s_2b_2 + 2s_1a_2)e_B^3 + \frac{3}{2}s_2a_2e_B^4 = \left[\frac{1+R(e_B)}{1-R(e_B)}\right]^2 [C_1(e_B) + t_1(e_B)]$$

$$t_1(e_C) = t_2(e_C) < t_2(e_A)$$
$$c_2 + (6s_1 + b_2)e_C + (3s_2c_2 + 3s_1b_2 + a_2)e_C^2 +$$
$$(2s_2b_2 + 2s_1a_2)e_C^3 + \frac{3}{2}s_2a_2e_C^4 = \left[\frac{1+R(e_C)}{1-R(e_C)}\right]^2 [C_1(e_C) + t_1(e_C)]$$

$$t_1(e_D) = t_2(e_D) < t_2(e_A)$$
$$c_2 + (6s_1 + b_2)e_D + (3s_2c_2 + 3s_1b_2 + a_2)e_D^2 +$$
$$(2s_2b_2 + 2s_1a_2)e_D^3 + \frac{3}{2}s_2a_2e_D^4 = \left[\frac{1+R(e_D)}{1-R(e_D)}\right]^2 [C_1(e_D) + t_1(e_D)]$$

Step 3. Measure the reflection information for the non-compressed state. In this state, the acoustic contrast between target medium and surrounding medium is typically lowest. Hence the boundary between the two media is less clear. However, by tracking the compression-enhanced boundary in the previous two steps, the boundary between the two media can be accurately estimated and the reflection coefficient can be computed.

$$\rho_2 C_2 = (e_i = 0) \left[\frac{1+R(e_i=0)}{1-R(e_i=0)}\right]^2 \rho_1 C_1(e_i = 0)$$

Step 4. Evaluate applied strains $e_A$, $e_B$, $e_C$ and $e_D$ using the relation (113).

Step 5. With evaluated strains $e_A$, $e_B$, $e_C$ and $e_D$, unknown material properties $$\left(s_1, s_2 \frac{b_2}{c_2} \text{ and } \frac{a_2}{c_2}\right)$$

can evaluated by solving the following two relations simultaneously. Again, the parameters on the right hand side of the relation are known or measured.

$$1 + \left(6s_1 + \frac{b_2}{c_2}\right)e_A + \left(3s_2 + 3s_1\frac{b_2}{c_2} + \frac{a_2}{c_2}\right)e_A^2 +$$
$$\left(2s_2\frac{b_2}{c_2} + 2s_1\frac{a_2}{c_2}\right)e_A^3 + \frac{3}{2}s_2\frac{a_2}{c_2}e_A^4 = \frac{\left[\frac{1+R(e_A)}{1-R(e_A)}\right]^2 [C_1(e_A) + t_1(e_A)]}{\left[\frac{1+R(e=0)}{1-R(e=0)}\right]^2 C_1(e=0)}$$

-continued $$1 + \left(6s_1 + \frac{b_2}{c_2}\right)e_B + \left(3s_2 + 3s_1\frac{b_2}{c_2} + \frac{a_2}{c_2}\right)e_B^2 + \left(2s_2\frac{b_2}{c_2} + 2s_1\frac{a_2}{c_2}\right)e_B^3 +$$

$$\frac{3}{2}s_2\frac{a_2}{c_2}e_B^4 = \frac{\left[\frac{1+R(e_B)}{1-R(e_B)}\right]^2 [C_1(e_B) + t_1(e_B)]}{\left[\frac{1+R(e=0)}{1-R(e=0)}\right]^2 C_1(e=0)}$$

$$1 + \left(6s_1 + \frac{b_2}{c_2}\right)e_C + \left(3s_2 + 3s_1\frac{b_2}{c_2} + \frac{a_2}{c_2}\right)e_C^2 + \left(2s_2\frac{b_2}{c_2} + 2s_1\frac{a_2}{c_2}\right)e_C^3 +$$

$$\frac{3}{2}s_2\frac{a_2}{c_2}e_C^4 = \frac{\left[\frac{1+R(e_C)}{1-R(e_C)}\right]^2 [C_1(e_C) + t_1(e_C)]}{\left[\frac{1+R(e=0)}{1-R(e=0)}\right]^2 C_1(e=0)}$$

$$1 + \left(6s_1 + \frac{b_2}{c_2}\right)e_D + \left(3s_2 + 3s_1\frac{b_2}{c_2} + \frac{a_2}{c_2}\right)e_D^2 + \left(2s_2\frac{b_2}{c_2} + 2s_1\frac{a_2}{c_2}\right)e_D^3 +$$

$$\frac{3}{2}s_2\frac{a_2}{c_2}e_D^4 = \frac{\left[\frac{1+R(e_D)}{1-R(e_D)}\right]^2 [C_1(e_D) + t_1(e_D)]}{\left[\frac{1+R(e=0)}{1-R(e=0)}\right]^2 C_1(e=0)}$$

Step 6. Set up four equations, by substituting evaluated two coefficients ($s_1$,$s_2$) for Poisson's ratio and any given strains say into eq.(207) and solve them simultaneously to retrieve three stiffness constants ($a_2$, $b_2$ and $c_2$):

$$t_1(e_A) = t_2(e_A)$$
$$= 6\left[s_1c_2e_A + \frac{1}{2}(s_2c_2 + s_1b_2)e_A + \frac{1}{3}(s_2b_2 + s_1a_2)e_A^3 + \frac{1}{4}s_2a_2e_A^4\right]$$

$$t_1(e_A) = t_2(e_A)$$
$$= 6\left[s_1c_2e_A + \frac{1}{2}(s_2c_2 + s_1b_2)e_A + \frac{1}{3}(s_2b_2 + s_1a_2)e_A^3 + \frac{1}{4}s_2a_2e_A^4\right]$$

$$t_1(e_A) = t_2(e_A)$$
$$= 6\left[s_1c_2e_A + \frac{1}{2}(s_2c_2 + s_1b_2)e_A + \frac{1}{3}(s_2b_2 + s_1a_2)e_A^3 + \frac{1}{4}s_2a_2e_A^4\right]$$

$$t_1(e_A) = t_2(e_A)$$
$$= 6\left[s_1c_2e_A + \frac{1}{2}(s_2c_2 + s_1b_2)e_A + \frac{1}{3}(s_2b_2 + s_1a_2)e_A^3 + \frac{1}{4}s_2a_2e_A^4\right]$$

Step. 7 Rebuild stiffness, Poisson's ratio and tangential modulus by:

$$C_2(e) = a_2 \cdot E^2 + b_2 \cdot e + c_2,$$
$$v(e) = \frac{1}{2} - (s_1 + s_2 \cdot e) \text{ and}$$
$$E(e) \approx 6\varphi(e) \cdot C(e) = 6(s_1 + s_2 \cdot e) \cdot (a_2 \cdot E^2 + b_2 \cdot e + c_2).$$

Step 8. Evaluate material density by:

$$\rho_2 = \rho_1 \frac{\left[\frac{1+R_0}{1-R_0}\right]^2 C_1(e_i = 0)}{t_1(e)} \left[6s_1e + \right.$$

$$\left.\left(3s_2 + 3s_1\frac{b_2}{c_2}\right)e^2 + \left(2s_2\frac{b_2}{c_2} + 2s_1\frac{a_2}{c_2}\right)e^3 + \frac{3}{2}s_2\frac{a_2}{c_2}e^4\right].$$

The discussion of ASG can be also applied to this technique. SGI can also use a stiffness function with any order and the form of function will not affect the basic concept of this technique.

Evaluation of Wave attenuation in a Deformed Medium

Figure 9:
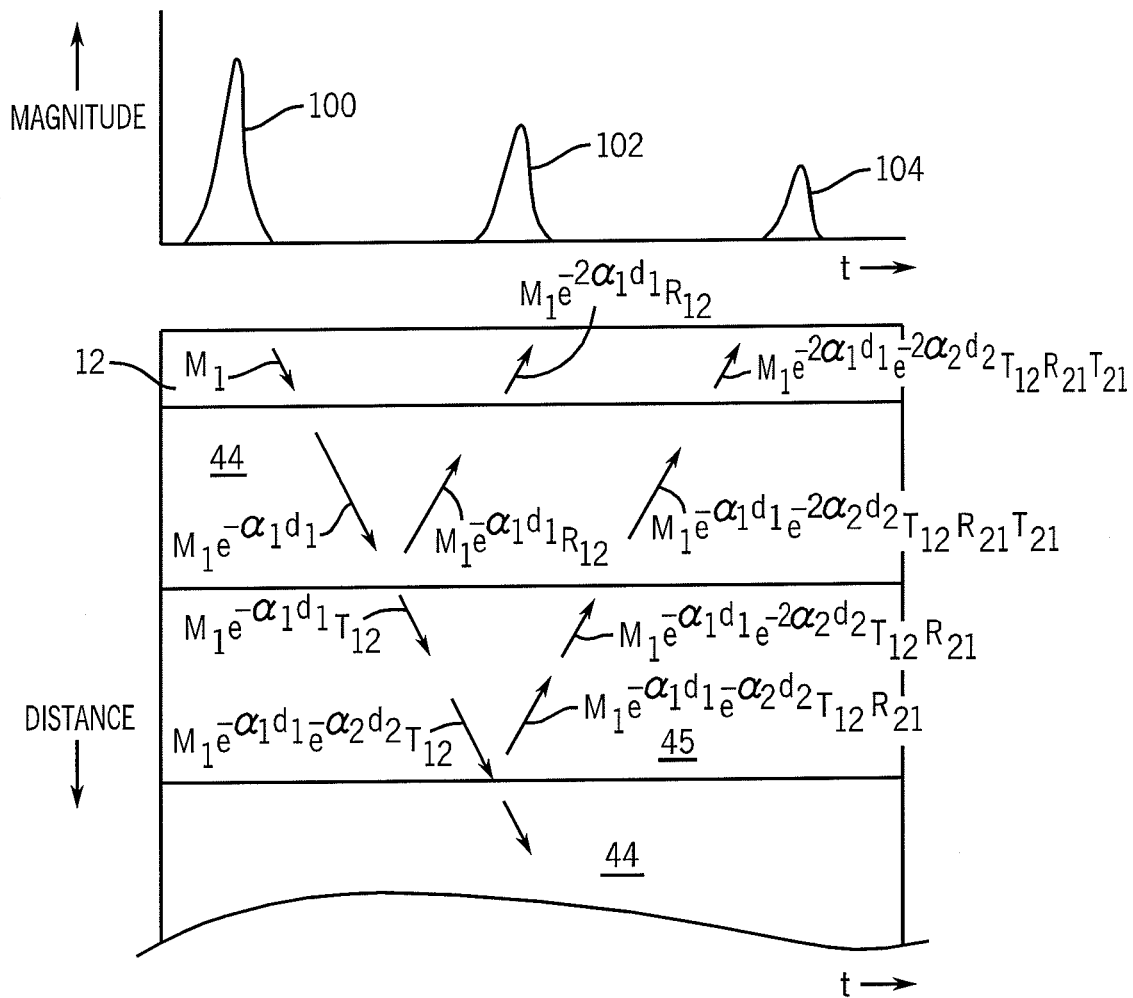
FIG. 9 is a diagram showing ultrasound waves and their magnitudes as they pass through the materials of FIGS. 2 and 3.

Referring now to FIG. 9, considering the passage of an input wave 100 to a target tissue (e.g. tendon 45 in FIG. 2 or tumor 18 in FIG. 1) and the resulting reflected waves. For simplicity in describing the method, only FIG. 2 application will be referenced in the remainder of this section with both the tumor and tendon referred to as the target 45 and the patient and coupling medium will be referred to as the medium 44. The input wave 100 with magnitude $M_I$ is attenuated to be $M_I e^{-a_1 d_1}$ when it arrives at the bottom of surrounding medium 44 (as depicted in FIG. 9) which has known attenuation coefficient $\alpha_2 = \alpha_1(e)$ and thickness $d_1 = d_1(e)$.

This wave is partially reflected at the near interface between surrounding medium 44 and the target 45 and changes its magnitude to $M_I e^{-a_1 d_1} R_{12}$ due to strain dependent reflection coefficient $R_{12} = R_{12}(e)$. The reflected wave travels though the thickness $d_1 = d_1(e)$ back to the surface. Therefore the wave magnitude is further attenuated to become $RW_1 = M_I e^{-2a_1 d_1} R_{12}$ and shows up as the first reflected wave 102 on the recorded data.

Now consider the passage of the input wave to generate the second reflected echo 104 in FIG. 9. A portion of the wave reaching the bottom of surrounding medium 44 (or 14) is transmitted into target 45. At this point, the magnitude of the input wave is $M_I e^{-a_1 d_1} T_{12}$ at the top of target 45, where $T_{12} = T_{12}(e)$ is defined as the transmission coefficient and indicates how much of the ultrasound signal passes from medium 44 into the target 45. This wave propagates to the bottom medium 44 on the lower side of the target 45 and at this interface reflects back up to the top of target 45. At the top of target 45, the wave magnitude is now attenuated to $M_I e^{-a_1 d_1} e^{-2a_2 d_2} T_{12} R_{21}$ through the attenuation property of the target 45 and the reflection coefficient at the bottom interface between the target 45 and surrounding medium 44. Since the wave in now propagating from the target toward the surrounding medium, a strain dependent reflection coefficient $R_{21} = R_{21}(e)$ is applied. Once again, the wave transmits back into the upper medium 44 and travels back to transducer 12 and shows up as the second reflected echo 104 in the recorded wave signal. Due to the reflection, transmission and attenuation, the second echo 104 has a magnitude of $RW_2 = M_I e^{-2a_1 d_1} e^{-2a_2 d_2} T_{12} R_{21} T_{21}$. Again, the wave in now propagating from target toward the surrounding medium a strain dependent transmission coefficient $T_{21} = T_{21}(e)$ is applied.

Since the magnitude of the first reflected echo and second reflected echo are expressed as combination of reflection coefficients and transmission coefficients, the relation between the reflection coefficient and transmission coefficient must be known. The following section defines how these basic relations are formulated in this method of analysis.

When a wave is propagating from medium 44 into the target 45, the reflection coefficient $R_{12}(e_i)$ at the interface of two media is given by $$R_{12}(e_i) = \frac{\rho_2 \cdot V_2(e_i) - \rho_1 \cdot V_1(e_i)}{\rho_2 \cdot V_2(e_i) + \rho_1 \cdot V_1(e_i)} = \frac{RW_1}{IW e^{-2\alpha_1 d_1}} \quad (300a)$$

In this relation, wave propagation velocity in the medium 44 and target 45 are represented by $V_1(e_i)$ and $V_2(e_i)$. Material density of both media are indicated by $\rho_1$ and $\rho_2$.

IW and $RW_1$ represent the magnitude of the input wave and the first reflected echo measured from recorded wave signal. Finally, the wave attenuation caused by medium 44 is expressed as $e^{-2\alpha_1 d_1}$. If wave attenuation in surrounding medium 44 can be ignored, the reflection coefficient at the near interface simplifies to $$R_{12}(e_i) = \frac{RW_1}{IW}.$$

The transmission coefficient $T_{12}(e_i)$ at the same interface is given by $$T_{12}(e_i) = \frac{2 \cdot \rho_2 \cdot V_2(e_i)}{\rho_2 \cdot V_2(e_i) + \rho_1 \cdot V_1(e_i)} \quad (300b)$$

In the reverse case (wave propagates from the target 45 into the medium 44), the reflection coefficient $R_{21}(e_i)$ and transmission coefficient $T_{21}(e_i)$ are given by $$R_{21}(e_i) = \frac{\rho_1 \cdot V_1(e_i) - \rho_2 \cdot V_2(e_i)}{\rho_2 \cdot V_2(e_i) + \rho_1 \cdot V_1(e_i)} \quad (300c)$$

and $$T_{21}(e_i) = \frac{2 \cdot \rho_2 \cdot V_1(e_i)}{\rho_2 \cdot V_2(e_i) + \rho_1 \cdot V_1(e_i)} \quad (300d)$$

By manipulating these relations, $R_{21}(e_i)$, $T_{12}(e_i)$ and $T_{21}(e_i)$ can be all expressed as the function of $R_{12\,(ei)}$ in following manner.

$$R_{21}(e_i) = -R_{12}(e_i),\ T_{12}(e_i) = 1 + R_{12}(e_i)\ \text{and}\ T_{21}(e_i) = 1 - R_{12}(e_i) \quad (300e)$$

These relations are then utilized as follows.

Evaluation of Wave Attenuation by Comparing first and Second Echo

The straight forward way of evaluating wave attenuation in the target 45 can be achieved by taking the ratio of the magnitudes of first reflected echo and second reflected by $$\frac{RW_1}{RW_2} = \frac{M_I e^{-2\alpha_1 d_1} R_{12}}{M_I e^{-2\alpha_1 d_1} e^{-2\alpha_2 d_2} T_{12} R_{21} T_{21}} \quad (301)$$

$$= \frac{R_{12}}{e^{-2\alpha_2 d_2}(1 + R_{12})(-R_{12})(1 - R_{12})}$$

$$= \frac{-1}{e^{-2\alpha_2 d_2}(1 - R_{12}^2)}$$

-continued or $$\left|\frac{RW_1}{RW_2}\right| = \left|\frac{-1}{e^{-2\alpha_2 d_2}(1 - R_{12}^2)}\right| = \frac{1}{e^{-2\alpha_2 d_2}(1 - R_{12}^2)}$$

due to $e^{-2\alpha_2 d_2} > 0$ and $(1 - R_{12}^2) > 0$.

In this derivation, relations (300e) were used.

From this ratio, the wave attenuation in the target 45 at any deformed configuration is $$\alpha_2(e) = \frac{1}{-2d_2(e)} \log\left[\left|\frac{RW_1(e)}{RW_2(e)}\right|(1 - R_{12}^2(e))\right] \quad (302)$$

In this relation, if the reflection is evaluated to be very small, this relation may be further simplified to $$\alpha_2(e) = \frac{1}{-2d_2(e)} \log\left[\left|\frac{RW_1(e)}{RW_2(e)}\right|\right] \quad (303)$$

If attenuation coefficient can be assumed to be a function of applied strain with a form of $$\alpha_2(e) = \gamma_1 \cdot e^2 + \gamma_2 \cdot e + \gamma_3 \quad (304)$$

then eq.(302) becomes:

$$\alpha_2(e) = \gamma_1 \cdot e^2 + \gamma_2 \cdot e + \gamma_3 \quad (305)$$

$$= \frac{1}{-2d_2(e)} \log\left[\left|\frac{RW_1(e)}{RW_2(e)}\right|(1 - R_{12}^2(e))\right]$$

In relation (304), $\gamma_1$, $\gamma_2$ and $\gamma_3$ represents the unknown attenuation constants to be determined from recorded wave signals.

Evaluation of Attenuation by Comparing Second Echo Measured at Different Strain $e_i$ The attenuation coefficient of target 45 can also be derived by comparing the second reflected echo measured at different strain levels. Say, second reflected echo is measured at strain level $e_i$ and $e_j$.

$$RW_2(e_i) = M_I e^{-2\alpha_1(e_i)d_1(e_i)} e^{-2\alpha_2(e_i)d_2(e_i)}(-R_{12}(e_i) + R_{12}^3(e_i)) \quad (306)$$

$$RW_2(e_j) = M_I e^{-2\alpha_1(e_j)d_1(e_j)} e^{-2\alpha_2(e_j)d_2(e_j)}(-R_{12}(e_j) + R_{12}^3(e_j)) \quad (307)$$

The ratio of these two echoes are given by, $$\frac{RW_2(e_i)e^{-2\alpha_1(e_j)d_1(e_j)}(-R_{12}(e_j) + R_{12}^3(e_j))}{RW_2(e_j)e^{-2\alpha_1(e_i)d_1(e_i)}(-R_{12}(e_i) + R_{12}^3(e_i))} = \quad (308)$$

$$\frac{e^{-2\alpha_2(e_i)d_2(e_i)}}{e^{-2\alpha_2(e_j)d_2(e_j)}} = e^{-2\alpha_2(e_i)d_2(e_i) + 2\alpha_2(e_j)d_2(e_j)}$$

If the attenuation and the thickness of the target medium can be considered small, then this relation can be further simplified to be $$\frac{RW_2(e_i)e^{-2\alpha_1(e_j)d_1(e_j)}(-R_{12}(e_j)+R_{12}^3(e_j))}{RW_2(e_j)e^{-2\alpha_1(e_i)d_1(e_i)}(-R_{12}(e_i)+R_{12}^3(e_i))} \approx \tag{309}$$

$$1-2\alpha_2(e_i)d_2(e_i)+2\alpha_2(e_j)d_2(e_j)$$

Applying a logarithmic operation to eq. (308) yields $$-2\alpha_2(e_i)d_2(e_i)+2\alpha_2(e_j)d_2(e_j) = \tag{310}$$

$$\log\left[\frac{RW_2(e_i)e^{-2\alpha_1(e_j)d_1(e_j)}(-R_{12}(e_j)+R_{12}^3(e_j))}{RW_2(e_j)e^{-2\alpha_1(e_i)d_1(e_i)}(-R_{12}(e_i)+R_{12}^3(e_i))}\right]$$

Substitution of eq.(304) into (310) results in the final relation to evaluate wave attenuation for this case, that is $$\gamma_1 \cdot [-2d_2(e_i) \cdot e_i^2 + 2d_2(e_j) \cdot e_j^2] + \tag{309}$$

$$\gamma_2 \cdot [-2d_2(e_i) \cdot e_i + 2d_2(e_j) \cdot e_j] + \gamma_3 \cdot [-2d_2(e_i) + 2d_2(e_j)] =$$

$$\log\left[\frac{RW_2(e_i)e^{-2\alpha_1(e_j)d_1(e_j)}(-R_{12}(e_j)+R_{12}^3(e_j))}{RW_2(e_j)e^{-2\alpha_1(e_i)d_1(e_i)}(-R_{12}(e_i)+R_{12}^3(e_i))}\right]$$

In this relation, the parameters on the right hand side either can be measured or can be evaluated from the steps described in previous sections.

If the magnitude of reflection coefficient $R_{12}(e_j)$ is very small and the higher term can be ignored, eq.(309) can be further simplified to:

$$\gamma_1 \cdot [-2d_2(e_i) \cdot e_i^2 + 2d_2(e_j) \cdot e_j^2] + \gamma_2 \cdot [-2d_2(e_i) \cdot e_i + 2d_2(e_j) \cdot e_j] + \tag{310}$$

$$\gamma_3 \cdot [-2d_2(e_i) + 2d_2(e_j)] \approx \log\left[\frac{RW_2(e_i)e^{-2\alpha_1(e_j)d_1(e_j)}(-R_{12}(e_j))}{RW_2(e_j)e^{-2\alpha_1(e_i)d_1(e_i)}(-R_{12}(e_i))}\right]$$

If the parameters $a_1(e_j)d_1(e_j)$ produce a relatively small amount of attenuation, then relation (309) can be further simplified to be $$1 + \gamma_1 \cdot [-2d_2(e_i) \cdot e_i^2 + 2d_2(e_j) \cdot e_j^2] + \tag{311}$$

$$\gamma_2 \cdot [-2d_2(e_i) \cdot e_i + 2d_2(e_j) \cdot e_j] + \gamma_3 \cdot [-2d_2(e_i) + 2d_2(e_j)] =$$

$$\frac{RW_2(e_i)e^{-2\alpha_1(e_j)d_1(e_j)}(-R_{12}(e_j))}{RW_2(e_j)e^{-2\alpha_1(e_i)d_1(e_i)}(-R_{12}(e_i))}$$

When the influence of the wave attenuation in surrounding medium 44 can be neglected ($e^{-2\alpha_1(e)d_1(e)} \approx 1$), relations (310) and (311) can be further simplified to be:

$$\gamma_1 \cdot [-2d_2(e_i) \cdot e_i^2 + 2d_2(e_j) \cdot e_j^2] + \gamma_2 \cdot [-2d_2(e_i) \cdot e_i + 2d_2(e_j) \cdot e_j] + \tag{312}$$

$$\gamma_3 \cdot [-2d_2(e_i) + 2d_2(e_j)] \approx \log\left[\frac{RW_2(e_i)(-R_{12}(e_j))}{RW_2(e_j)(-R_{12}(e_i))}\right]$$

and $$1 + \gamma_1 \cdot [-2d_2(e_i) \cdot e_i^2 + 2d_2(e_j) \cdot e_j^2] + \tag{313}$$

$$\gamma_2 \cdot [-2d_2(e_i) \cdot e_i + 2d_2(e_j) \cdot e_j] +$$

$$\gamma_3 \cdot [-2d_2(e_i) + 2d_2(e_j)] = \frac{RW_2(e_i)(-R_{12}(e_j))}{RW_2(e_j)(-R_{12}(e_i))}$$

The thickness of target 45 is treated as known parameter through this derivation. The target 44 thickness for ASG case can be given by eq.(14) based on a known target medium density and eq. (217) for SGI based on the condition of stress continuity.

(Implementation)

Step 1. Measure wave signals at multiple different unknown strain levels and evaluate reflection coefficients $R_{12}$(e) and target medium thicknesses $d_2$(e) at each strain level.

For attenuation evaluations based on eq.(305), three separate measurements are required.

Yet four sets of measurements are required for evaluation based on eq. (309).

In ASG, the target medium thickness should be evaluated by eq. (14). The thickness of target medium in SGI should be evaluated by eq. (217).

Step 2. Set up system of equations for attenuation constants ($\gamma_1$, $\gamma_2$ and $\gamma_3$) evaluation.

For technique based on eq. (305), following three equations are required:

$$\gamma_1 \cdot e_A^2 + \gamma_2 \cdot e_A + \gamma_3 = \frac{1}{-2d_2(e_A)}\log\left[\left|\frac{RW_1(e_A)}{RW_2(e_A)}\right|(1-R_{12}^2(e_A))\right]$$

$$\gamma_1 \cdot e_B^2 + \gamma_2 \cdot e_B + \gamma_3 = \frac{1}{-2d_2(e_B)}\log\left[\left|\frac{RW_1(e_B)}{RW_2(e_B)}\right|(1-R_{12}^2(e_B))\right]$$

$$\gamma_1 \cdot e_C^2 + \gamma_2 \cdot e_C + \gamma_3 = \frac{1}{-2d_2(e_C)}\log\left[\left|\frac{RW_1(e_C)}{RW_2(e_C)}\right|(1-R_{12}^2(e_C))\right]$$

For technique based on eq.(309), following three equations are utilized:

$$\gamma_1 \cdot [-2d_2(e_A) \cdot e_A^2 + 2d_2(e_B) \cdot e_B^2] +$$

$$\gamma_2 \cdot [-2d_2(e_A) \cdot e_A + 2d_2(e_B) \cdot e_B] + \gamma_3 \cdot [-2d_2(e_A) + 2d_2(e_B)] =$$

$$\log\left[\frac{RW_2(e_A)e^{-2\alpha_1(e_B)d_1(e_B)}(-R_{12}(e_B)+R_{12}^3(e_B))}{RW_2(e_B)e^{-2\alpha_1(e_A)d_1(e_A)}(-R_{12}(e_A)+R_{12}^3(e_A))}\right]$$

$$\gamma_1 \cdot [-2d_2(e_A) \cdot e_A^2 + 2d_2(e_C) \cdot e_C^2] +$$

$$\gamma_2 \cdot [-2d_2(e_A) \cdot e_A + 2d_2(e_C) \cdot e_C] + \gamma_3 \cdot [-2d_2(e_A) + 2d_2(e_C)] =$$

$$\log\left[\frac{RW_2(e_A)e^{-2\alpha_1(e_C)d_1(e_C)}(-R_{12}(e_C)+R_{12}^3(e_C))}{RW_2(e_C)e^{-2\alpha_1(e_A)d_1(e_A)}(-R_{12}(e_A)+R_{12}^3(e_A))}\right]$$

$$\gamma_1 \cdot [-2d_2(e_A) \cdot e_A^2 + 2d_2(e_D) \cdot e_D^2] +$$

$$\gamma_2 \cdot [-2d_2(e_A) \cdot e_A + 2d_2(e_D) \cdot e_D] + \gamma_3 \cdot [-2d_2(e_A) + 2d_2(e_D)] =$$

$$\log\left[\frac{RW_2(e_A)e^{-2\alpha_1(e_D)d_1(e_D)}(-R_{12}(e_D)+R_{12}^3(e_D))}{RW_2(e_D)e^{-2\alpha_1(e_A)d_1(e_A)}(-R_{12}(e_A)+R_{12}^3(e_A))}\right]$$

Step 3. Solve the system of equations simultaneously to evaluate three constants $\gamma_1$, $\gamma_2$ and $\gamma_3$.

Figure 7:
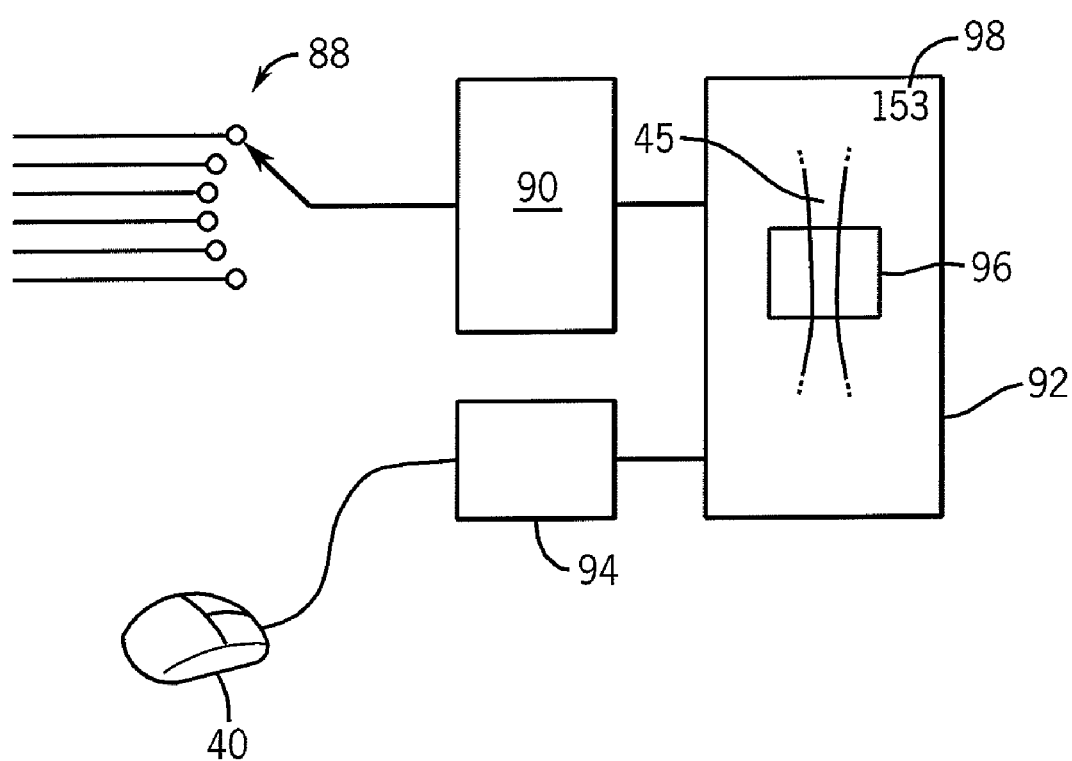
FIG. 7 is a block diagram of a mapping system used to provide images and quantitative information from the systems of FIGS. 4 and 6.

Referring to FIG. 7, each of these output values of stiffness, stiffness at no compression, density and wave attenuation, may be provided selectively or in combination by a selector means 89 implemented, for example within the program 72, which is provided to a mapper program 90, which maps the values of individual ones or combinations of strain 78 and material properties 74 including: stiffness gradient 82, initial stiffness 84, density 86 or wave attenuation 88 to a color or gray scale to produce a graphic image 92 on the display 36 of FIG. 1. The cursor control device 40 operating through a driver program 94 may allow for the placement of a region of interest cursor 96 on the image to direct the processor 33 to make a quantitative measurement display 98 of the tissue within the region of the cursor 96. Location of the cursor 96 may, for example, be with respect to a standard B mode image obtained by the acoustoelastographic ultrasound system 10 or may be an image produced by any of the quantities described above. Selector means 89 may also include an input for standard B mode data.

Figure 8:
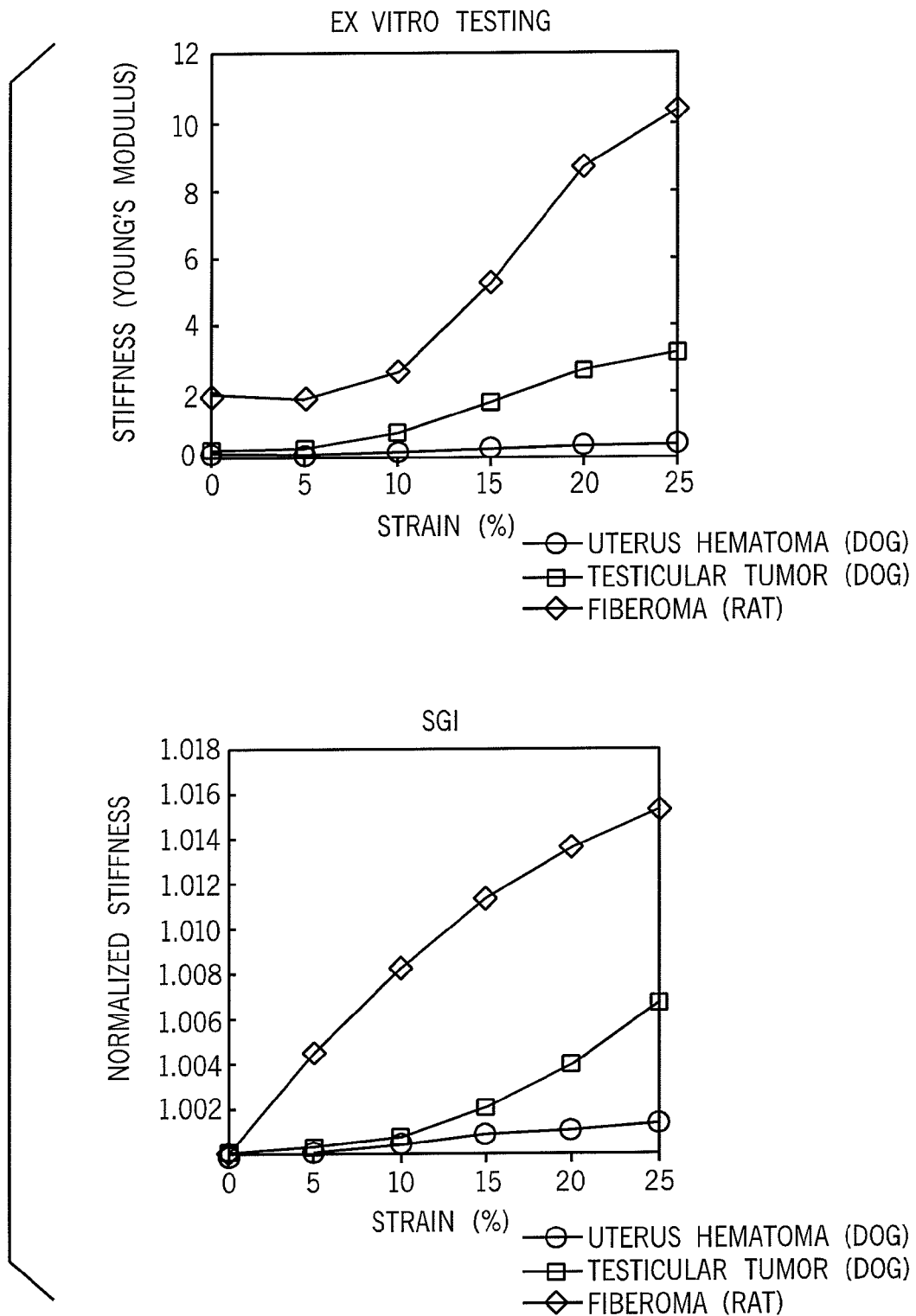
FIG. 8 is a pair of graphs showing stiffness gradient determined using the present invention and per ex vitro measurement showing the performance of the present invention and the ability of stiffness gradient to distinguish tissue types.

Referring now to FIG. 8, experimental results have shown that the SGI technique is able to differentiate among tissue types that exhibit different stiffness gradients, that is, changes in stiffness as a function of strain that closely correspond to stiffness gradients actually tested ex vitro with a standard material testing machine. This ability to measure stiffness gradient offers the potential for better differentiation of tissue types.

Both ASG and SGI are examples of techniques that use acoustoelastic theory and information from both the reflection coefficient and wave propagation time (measured from a number of loaded states and an unloaded state) to compute strains and material properties. If the properties of the surrounding medium (or tissue) are unknown, this method could be used to compute the properties of the surrounding medium first (in comparison to a known coupling material). Then the target tissue can be serially analyzed and identified in comparison to the now known behavior of the surrounding medium.

These methods could be used for materials other than biological tissues.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ultrasound system for measuring strain with ultrasound in a material subject to varying tension, the system comprising:
   an ultrasound transducer assembly for transmitting an acoustic ultrasound signal into the material along a first axis and receiving the acoustic ultrasound signal after reflection and modification by the material adapted to obtain a first and second echo signal from a first and second material location when the material is at a first and second tension applied along a second axis substantially perpendicular to the first axis, the first and second echo signals being electrical representations of portions of the ultrasound signal after reflection and modification by the material, the electrical representations being produced by the ultrasound transducer assembly by conversion of the acoustic ultrasound signal after reflection and modification into the electrical representations; and
   a processor in electrical communication with the ultrasound transducer assembly to receive the first and second echo signal from the ultrasound transducer assembly and processing the first and second echo signals according to a stored program to deduce both absolute strain of the material and material stiffness without a previous determination of the amount of tension;
   wherein the processor determines strain and material stiffness from a time of flight of ultrasound between a first and second interface in the material and a reflection coefficient indicating relative strength of reflected ultrasonic energy with respect to incident ultrasonic energy.

2. A system for measuring material properties with ultrasound of a material subject to varying deformation, the system comprising:
   an ultrasound transducer assembly for transmitting an acoustic ultrasound signal into a material and receiving the acoustic ultrasound signal after reflection and modification by the material; and
   a processor communicating with the ultrasound transducer assembly to receive an electrical ultrasound signal corresponding to the received acoustic ultrasound signal as modified by the material and processing the electrical ultrasound signal according to a stored program executing to:
   (i) measure a relative reflection strength of the electrical ultrasound signal as indicates relative strength of reflected waves of the acoustic ultrasound signal in the material under a first and second deformation of the material at a first and second boundary of the material with respect to incident waves of the acoustic ultrasound signal;
   (ii) measure a time of travel of the acoustic ultrasound signal between the first and second boundary by analysis of the electrical ultrasound signal; and
   (iii) combine the relative reflection strength and time of travel to deduce at least one property selected from the group consisting of material strain, material stiffness at one state of deformation, stiffness gradient of the material with respect to strain, material density, material Poisson's ratio, material tangential modulus, target tissue thickness as a function of applied strain and wave attenuation of the material as a function of applied strain.

3. The ultrasonic elastography system of claim 2 wherein the program is adapted to provide the at least one property when the deformation is a compression applied to the material along an axis of ultrasound transmission.

4. The ultrasonic elastography system of claim 3 wherein the deduced property is stiffness gradient as a function of strain.

5. The ultrasonic elastography system of claim 3 wherein the deduced property is stiffness for a non-deformed state of the material.

6. The ultrasonic elastography system of claim 3 wherein the deduced property is density of the material.

7. The ultrasonic elastography system of claim 3 wherein the deduced property is the Poisson's ratio of the material as function of applied strain.

8. The ultrasonic elastography system of claim 3 wherein the deduced property is the tangential modulus of the material as function of strain applied along an axis substantially perpendicular to an axis of propagation of the acoustic ultrasound signal.

9. The ultrasonic elastography system of claim 8 wherein the program is adapted to provide the at least one property when the material is an in vivo tendon.

10. The ultrasonic elastography system of claim 3 wherein the deduced parameter is the target tissue thickness as function of strain applied along an axis substantially perpendicular to an axis of propagation of the acoustic ultrasound signal.

11. The ultrasonic elastography system of claim 3 wherein the deduced property is a wave attenuation of the material as function of strain applied along an axis substantially perpendicular to an axis of propagation of the acoustic ultrasound signal.

12. The ultrasonic elastography system of claim 2 wherein the deformation is a tension applied to the material across an axis of ultrasound transmission and wherein the deduced property is strain of the material.

13. The ultrasonic elastography system of claim 2 wherein the processor does not employ an independent measure of a force of deformation.

14. The ultrasonic elastography system of claim 2 wherein the reflection strength is a measure of a relative power reflected at the boundary.

15. The ultrasonic elastography system of claim 2 wherein step (i) divides the received ultrasonic signal into time periods related to the first and second reflected waves and compares signal strength in a limited frequency range.

16. The ultrasonic elastography system of claim 2 wherein the material is a material to be measured surrounded by a transmission material.

17. The ultrasonic elastography system of claim 2 further including a display and wherein the processor provides an output of the deduced property as an image on the display characterizing the material according to the deduced property.

18. A method of measuring material properties with ultrasound comprising the steps of:

(a) using an ultrasound transducer assembly to transmit an acoustic ultrasound signal into the material and receive the acoustic ultrasound signal after modification by the material; and (b) receiving from the ultrasound transducer at a computer processor an electrical signal representing the ultrasound signal modified by the material from the ultrasound transducer and processing the electrical signal to:
  (i) measure a relative reflected strength of reflected waves of the acoustic ultrasound signal with respect to an incident strength of incident waves of the acoustic ultrasound signal under a first and second deformation of the material at a first and second boundary of the material;
  (ii) measure a time of travel of the waves of the acoustic ultrasound signal between the first and second boundary; and
  (iii) combine the relative reflected strength and time of travel to deduce at least one property selected from the group consisting of material strain, material stiffness at one state of deformation, stiffness gradient of the material with respect to strain, material density, material Poisson's ratio, material tangential modulus, target tissue thickness and wave attenuation of the material.

* * * * *